(12) United States Patent  (10) Patent No.: US 10,240,596 B2
Wandel                    (45) Date of Patent:     Mar. 26, 2019

(54) STERILIZABLE PUMP UNIT

(71) Applicant: Erbe Elektromedizin GmbH, Tuebingen (DE)

(72) Inventor: Waldemar Wandel, Kusterdingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 169 days.

(21) Appl. No.: 14/667,199

(22) Filed: Mar. 24, 2015

(65) Prior Publication Data
US 2015/0272605 A1 Oct. 1, 2015

(30) Foreign Application Priority Data
Mar. 26, 2014 (EP) .................................... 14161813

(51) Int. Cl.
F04B 53/10 (2006.01)
F16K 39/02 (2006.01)
(Continued)

(52) U.S. Cl.
CPC ...... *F04B 53/1025* (2013.01); *A61B 17/3203* (2013.01); *F04B 1/02* (2013.01);
(Continued)

(58) Field of Classification Search
CPC .... F04B 53/1025; F04B 53/1022; F04B 1/02; F04B 23/06; F16K 39/02; F16K 1/446;
(Continued)

(56) References Cited

U.S. PATENT DOCUMENTS 3,039,488 A * 6/1962 Bowerman ......... F04B 53/1025
                                            137/516.29
4,188,174 A * 2/1980 Perkins ................ F04B 53/102
                                            137/246.22
(Continued)

FOREIGN PATENT DOCUMENTS

CN    101374567 A   2/2009
DE    102006053609 A1  5/2008
(Continued)

OTHER PUBLICATIONS

European Search Report in corresponding European Application No. 14161813, dated Sep. 19, 2014, 6 pages.
(Continued)

*Primary Examiner* — Bryan Lettman
(74) *Attorney, Agent, or Firm* — Fitch, Even, Tabin & Flannery LLP

(57) ABSTRACT

The pump unit (10) has a particularly simple design, which includes just two housing parts (14, 15) and also four valve closure members (37) and pump pistons (25, 29). The valve closure members (37) are preferably identical to one another and are trapped in a pocket between both housing parts (14, 15). The housing parts (14, 15) are preferably permanently interconnected by an ultrasonic weld seam. The valve closure members are formed by disc-like or plate-like plastic parts, which are resilient per se and which may optionally have a central pin (42) as an assembly and orientation aid. As desired, the valve closure members bear against their respective valve seat (43) with or without bias and form valves which open and close particularly reliably, are responsive to the slowest flow velocities and can be easily sterilized.

20 Claims, 2 Drawing Sheets

(51) Int. Cl.
    *F16K 21/02* (2006.01)
    *F16K 1/44* (2006.01)
    *F04B 1/02* (2006.01)
    *F04B 1/04* (2006.01)
    *F04B 53/00* (2006.01)
    *A61B 17/3203* (2006.01)

(52) U.S. Cl.
    CPC .......... *F04B 1/0452* (2013.01); *F04B 53/007* (2013.01); *F16K 1/446* (2013.01); *F16K 21/02* (2013.01); *F16K 39/02* (2013.01); *F04B 53/1087* (2013.01)

(58) Field of Classification Search
    CPC ...... F16K 21/02; F16K 15/141; F16K 15/142; Y10T 137/7888; Y10T 137/789
    See application file for complete search history.

(56) References Cited

U.S. PATENT DOCUMENTS

| | | | | |
|---|---|---|---|---|
| 4,904,236 | A | * | 2/1990 | Redmond .......... A61M 27/006 137/854 |
| 4,958,661 | A | * | 9/1990 | Holtermann .......... F16K 15/141 137/843 |
| 5,392,694 | A | * | 2/1995 | Muller .................... A47J 31/36 99/295 |
| 6,682,325 | B1 | | 1/2004 | Beck |
| 8,083,493 | B2 | | 12/2011 | Hagg et al. |
| 8,251,679 | B2 | | 8/2012 | Kuehner et al. |
| 2009/0018513 | A1 | | 1/2009 | Fujii et al. |
| 2009/0166575 | A1 | * | 7/2009 | Bereznai ................. F16K 21/02 251/368 |
| 2010/0049228 | A1 | * | 2/2010 | Kuehner ............ A61B 17/3203 606/167 |
| 2011/0091331 | A1 | | 4/2011 | Moutafis et al. |
| 2014/0079580 | A1 | | 3/2014 | Häbe |

FOREIGN PATENT DOCUMENTS

| | | |
|---|---|---|
| EP | 2491968 A1 | 8/2012 |
| EP | 2711545 A1 | 3/2014 |
| JP | 200351549 A | 5/2003 |
| JP | 2004344442 A | 12/2004 |
| JP | 2007507261 A | 3/2007 |
| JP | 2008045698 A | 2/2008 |
| JP | 2008256606 A | 10/2008 |
| JP | 2010509542 A | 3/2010 |
| JP | 2010073541 A | 4/2010 |
| WO | 0140042 A1 | 6/2001 |
| WO | 2005034777 A1 | 4/2005 |

OTHER PUBLICATIONS

Office action and search report in corresponding Chinese application No. 2016082302079800, dated Aug. 26, 2016, 16 pages.
Office action in corresponding Japanese application No. 2015-065013, dated Aug. 16, 2016, 6 pages.
Office action in corresponding Korean application No. 10-2015-0037491, dated Jul. 27, 2016, 7 pages.

* cited by examiner

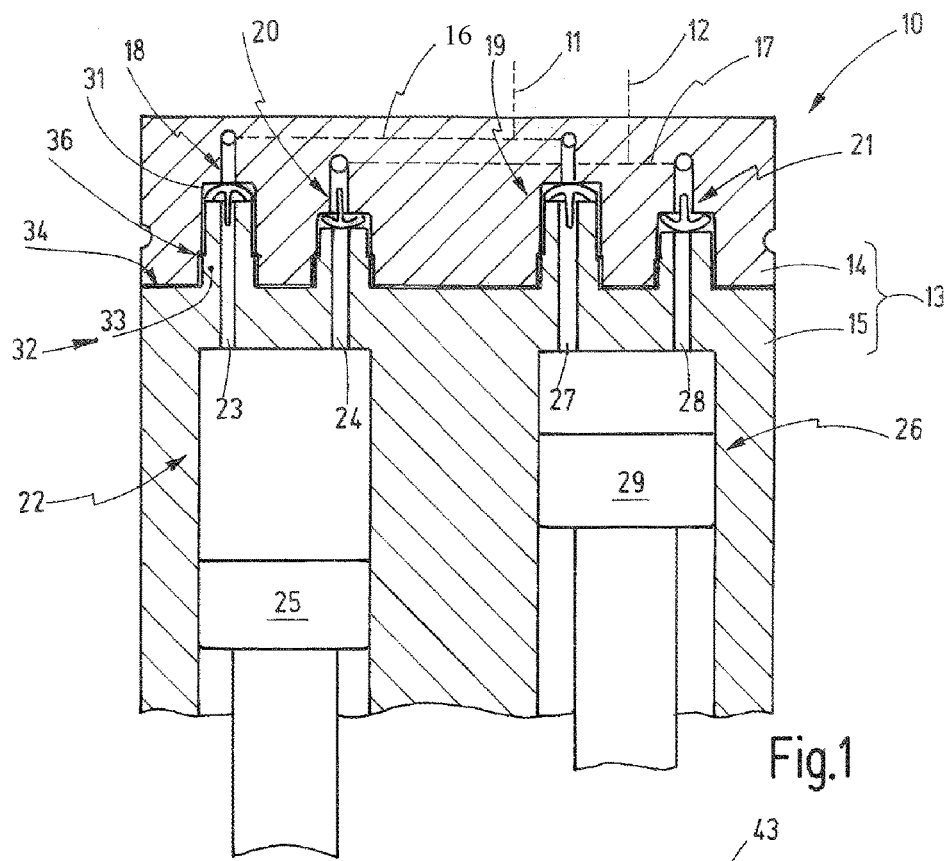
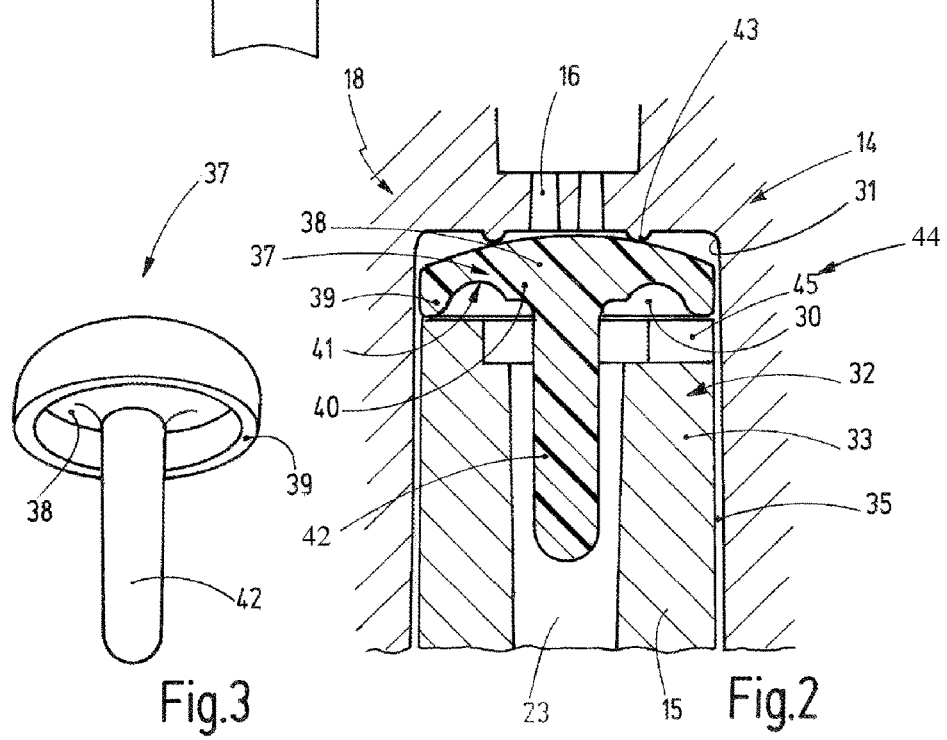

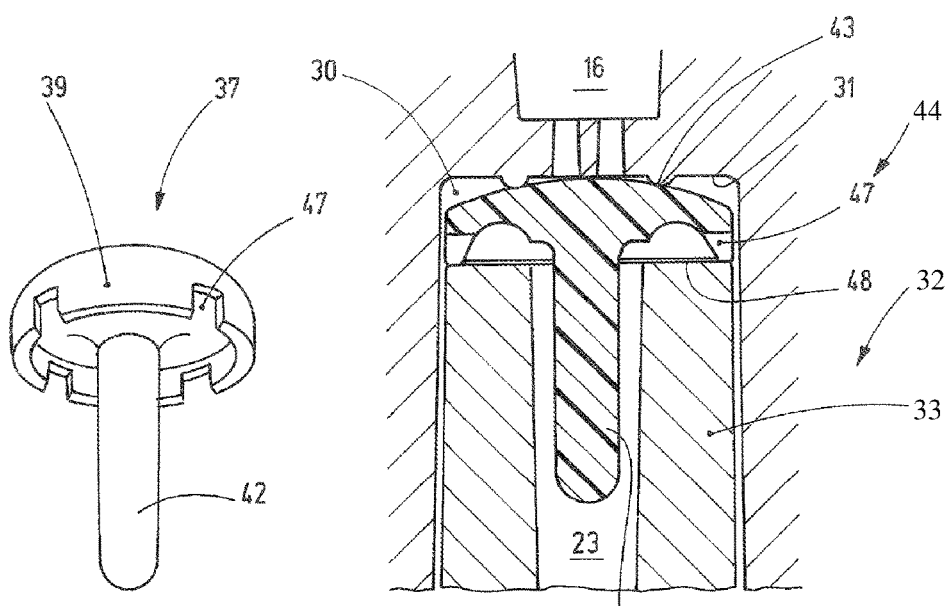
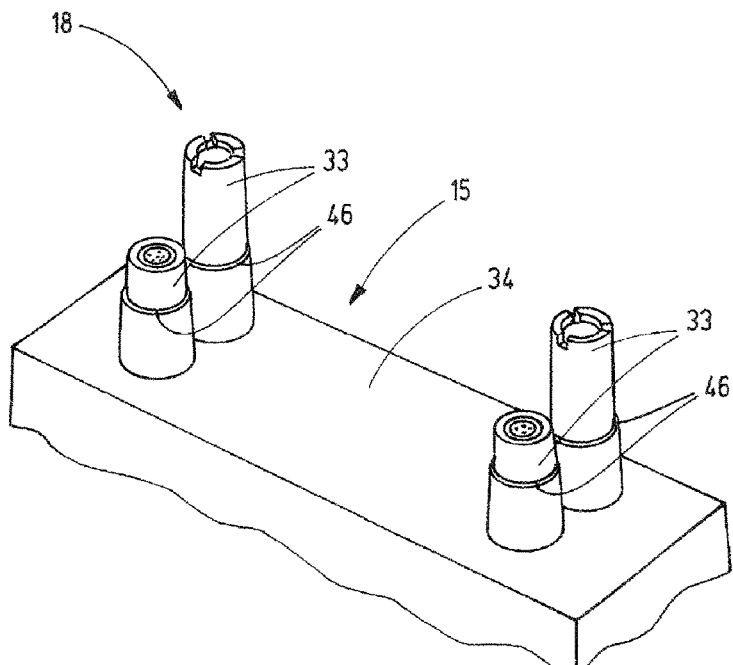

STERILIZABLE PUMP UNIT

RELATED APPLICATION(S)

This application claims the benefit of European Patent Application No. EP 14161813.2 filed Mar. 26, 2014, the contents of which are incorporated herein by reference as if fully rewritten herein.

TECHNICAL FIELD

The invention relates to a pump unit, in particular for medical use, especially for water jet surgery.

BACKGROUND

In the case of water jet surgery, a jet of physiological saline solution is directed onto a biological tissue by a suitable instrument, said tissue being completely or partially cut and/or severed. Gentle operation techniques are thus possible. The corresponding instrument has to be supplied with the treatment fluid, in particular NaCl solution, at the desired pressure and/or desired delivery volume. For this purpose, a pump unit is used in the prior art that typically has two separately driven pump pistons working in opposite directions. It is thus ensured via corresponding inlet and outlet valves that the pump pistons suck in NaCl solution and deliver this in a manner directed towards the instrument.

Such pump units are provided sterile, for example as disposable articles. The pump unit is a medical sterile product. This requires that the pump unit be produced under particular cleanliness requirements, for example in a clean room, and cleaned after assembly where appropriate. In particular, the pump unit must be sterilised following assembly. To this end, gas sterilisation methods can be used in which appropriate sterilisation gases, such as ethylene oxide, formaldehyde, peracetic acid or the like, are guided through the channels of the pump unit. However, since the pump unit is configured to convey liquids, but not to convey gases, it is a challenge to ensure that the sterilisation gas used actually reaches all relevant points of the pump unit.

A further problem with the pump units arises due to the required large range of adjustable delivery volumes. Both with quick and also in particular with very slow piston movement, a uniform, non-pulsating, continuous NaCl jet must be produced. This places particular requirements on the inlet and outlet valves of the pump unit.

SUMMARY

On this basis, the object of the invention is to specify an improved pump unit.

The pump unit has a pump housing that has at least one first and one second housing part. The pump housing preferably consists merely of the first and the second housing part. Whereas one of the housing parts has pump cylinders for receiving pump pistons, the other housing part is provided with a suction channel and a pressure channel. In addition, valve chambers are formed in the pump housing, in which valve chambers there are arranged valve closure members. The valve chambers are formed by valve chamber recesses and valve chamber closures. Whereas a valve chamber recess is arranged in one of the housing parts, the associated valve chamber closure can be formed on the other housing part. The valve chambers, that is to say the valve housings, are thus formed by the pump housing itself. For example, all valve chamber recesses may be formed in the first housing part and all valve chamber closures may be formed on the second housing part. A simple structure that is easy to assemble is provided, with which all inlet and outlet valves are completed when the housing parts are joined together.

The valve closure member is permeable to sterilisation gas. It consists for example of a plate or disc made of a suitable plastic, such as silicone or an elastomer, for example EPM, EPDM, FPM or the like. Due to the cooperation of geometric shape, that is to say thin-walled geometry of the valve closure member, and material selection thereof, low-molecular sterilisation gases can penetrate through the valve closure member at a sufficient rate and can thus reach the inner channels of the ump unit, without having to be pressed through the pump unit with pressure application. In particular, the valve closure member bears against the associated valve seat without bias or with little bias. Valve springs or the like are preferably not provided. The resulting low surface pressure at the valve seat prevents the valve closure member from adhering to the valve seat, as a suction valve in particular also enables liquids to be sucked in at a very low flow rate (flow velocity), and promotes sterilisation. Only extremely low forces for opening the valve are therefore necessary, and thus only extremely small pressure differences are necessary at the valve in order to open said valve.

The pump unit preferably has a valve closure member that is approximately T-shaped in cross section, that is to say has a plate portion and a central pin. The central pin may extend into the suction channel, the pressure channel or the pump channel. In particular if the plate portion of the valve closure member is formed asymmetrically with respect to a radial plane, the central pin constitutes an essential assembly aid. In addition, it ensures when guiding the housing parts together that the valve closure members are correctly positioned and are not damaged when the housing parts are brought together.

The valve closure member preferably has a rigid hub portion, a relatively rigid edge, and an intermediately arranged spring portion, which connects the edge to the hub portion resiliently. The edge has a smaller diameter than the valve chamber recess, such that a flow-permeable annular gap is formed between these two parts. Alternatively, overflow pockets can be formed in the wall of the valve chamber recess.

The spring zone is preferably a resilient ring zone formed by a groove, the material thickness of the plate portion as measured in the axial direction being less than at other points of the plate portion. The groove surrounds the hub portion preferably concentrically. The hub portion can thus move axially resiliently with respect to the edge. The plate portion is preferably convexly curved on the side facing a valve seat. In addition, the annular spring zone preferably has a diameter that is at least as large as an annular valve seat associated with the valve closure member.

The valve chambers are formed as described between the valve chamber recess and the valve chamber closure. The valve chamber closures are preferably formed as extensions protruding into the valve chamber recess. The extensions can sit in the valve chamber recess with or without play. In a preferred embodiment, an annular gap is formed between the outer peripheral surface of the valve chamber closure, which outer peripheral surface for example is cylindrical or slightly conical, and the corresponding opposite surface of the valve chamber recess. This annular gap is at least so wide that it enables an at least small radial movability of the housing parts relative to one another, until they are interconnected. The movability is fixed such that the housing parts can be interconnected by an extensive integrally bonded connection, in particular in a friction welding method, for example an ultrasonic welding method.

Since the valve chamber closures are formed on extensions which protrude beyond the plane determined by the friction weld seam, the valve chamber is not affected by any deformations or material beads forming from the friction welding process.

The valve closure members of the individual valve arrangements are preferably uniform, that is to say are identical to one another. However, they may also be formed differently from one another. Each valve closure member, in a central region, has a seal portion, whereas a structure over which the liquid flows is fixed on the peripheral edge of the valve closure member or on a structure of the pump housing arranged adjacently to said peripheral edge. This structure over which the liquid flows can be included by one or more recesses penetrating the edge of the valve closure member or can be formed by recesses in the adjacent bearing surface of the valve closure member.

The valve closure member of at least one of the valves is preferably arranged in a manner bearing against the valve seat without play. Here, it is itself slightly deformable so as to be able to resiliently release the channel controlled thereby. All valves can be formed in accordance with this design. It is possible to arrange all valve closure members of all valves in a manner bearing with identical bias against the valve seats thereof. Alternatively, it is also possible to allow the valve closure members of different valves to bear against the valve seats thereof with different biases. For example, the valve closure members of the inlet valves can bear against the valve seats with lower bias or a bias of zero or with play, whereas the valve closure members of the outlet valves can bear against the valve seats thereof with greater bias.

Further details of advantageous embodiments of the invention are specified in the description, the drawing or claims. In the drawing:

BRIEF DESCRIPTION OF THE DRAWINGS

FIG. 1 shows a pump unit according to the invention in a schematic vertical sectional illustration.

FIG. 2 shows an inlet valve of the pump unit according to FIG. 1 in an enlarged vertical sectional illustration.

FIG. 3 shows a valve closure member of the pump unit according to FIGS. 1 and 2.

FIG. 4 shows a modified embodiment of an inlet valve of the pump unit corresponding to FIG. 1 in a vertical sectional illustration.

FIG. 5 shows the valve closure member of the inlet valve according to FIG. 4 in a perspective illustration, and FIG. 6 shows the second housing part of the pump unit according to FIG. 1 in a simplified perspective illustration.

DETAILED DESCRIPTION

FIG. 1 illustrates a pump unit 10 that is intended for medical use. It can be used for example as a pump for NaCl solution for water jet surgery. It sucks in NaCl solution or another desired liquid at a connection 11 indicated in a dashed manner in FIG. 1 and conveys this via a connection 12, likewise merely indicated schematically, to a water jet surgery instrument.

The pump unit 10 has a housing 13, which consists of a first housing part 14 and a second housing part 15. The housing 13 preferably consists merely of these two housing parts, which are fixedly interconnected, preferably non-detachably. The housing parts 14, 15 preferably consist of a plastic, preferably a plastic suitable for ultrasonic welding.

A suction channel 16 connected to the connection and a pressure channel 17 connected to the connection 12 are formed in the first housing part 14. The suction channel 16 leads to suction valves 18, 19. The pressure channel 17 is connected to outlet valves 20, 21.

The inlet valve 18 and the outlet valve 20 are associated with the first pump cylinder 22, which is connected to the inlet valve 18 via a pump channel 23 and to the outlet valve 20 via a pump channel 24. A pump piston 25 is arranged in the first pump cylinder 22 and can be connected via a coupling (not illustrated in greater detail) to a drive device in order to be moved in the pump cylinder 22 in a controlled manner pumping to and fro.

A second pump cylinder 26 is also arranged in the second housing part 15 and is connected via pump channels 27, 28 to the inlet valve 19 and the outlet valve 21. A pump piston 29 is arranged in the pump cylinder 26 and can be connected via a coupling device (not illustrated in greater detail) to the drive device. The drive device ensures that the pump pistons 25, 29 are moved in opposite directions, such that the liquid to be conveyed is sucked in uniformly via the suction channel 16 and is delivered uniformly via the pressure channel 17. The drive device is preferably formed here such that it can move the pump pistons 25, 29 in opposite directions at variable speeds and/or variable strokes in order to adjust the delivery volume and the delivery pressure of the conveyed liquid within wide limits as desired.

The liquid inflow and outflow into and out from the two pump cylinders 22, 26 controls the inlet valves 18, 19 and the outlet valves 20, 21, which are check valves. For a further explanation of the nature of these valves, reference is made representatively for the other valves 19, 20, 21 to the inlet valve 18 below with reference to FIG. 2.

The inlet valve 18 includes a valve chamber 30, which is connected to the suction channel 16 and the pump channel 23. The suction channel 16 and the pump channel 23 are preferably arranged on opposite sides of the valve channel 30.

In order to form the valve chamber 30, one of the housing parts, here for example the first housing part 14, has a valve chamber recess 31, which is associated with a valve chamber closure 32 provided on the respective other housing part, here the second housing part 15. The valve chamber closure 32 is formed in the present exemplary embodiment by a pin-like extension 33, which protrudes starting from an upper end face 34 of the second housing part 15 into the valve chamber recess 31. The pump channel 23 extends through the extension 33 and leads into the end face thereof.

As can be seen in FIGS. 1 and 6, the extension 33 can be formed cylindrically or also (very slightly) conically. Its approximately cylindrical outer peripheral surface can bear against the inner wall of the valve chamber recess 31 or, together therewith, can define an annular gap 35, as illustrated in FIG. 2. The two housing parts 14, 15 are tightly interconnected, such that the valve chamber 30 communicates with the suction chamber 16 and the pump channel 23, but is otherwise tight. It is possible to produce the seal by means of a press fit of the extension 33 in the valve chamber recess 31. The seal can also be caused by a separate seal element, for example a ring seal. The seal, however, is preferably produced by an integrally bonded connection, in particular a friction weld seam 36, in particular in the form of an ultrasonic weld seam, which surrounds each extension 33 annularly at the entire periphery thereof. To this end, the extension 33 can be stepped in the gap 35 thereof different from zero, and the valve chamber recess 31 may also have an annular shoulder. If the housing parts 14, 15 are joined together and exposed to ultrasound, the annular gap 35 ensures sufficient transverse movability in order to form the ultrasonic or friction weld seam 36 between the step and the annular shoulder. This weld seam is preferably arranged at a distance from the valve chamber 30 in all embodiments.

A valve closure member 37 is arranged in the valve chamber 30. This is illustrated separately in FIG. 3. The valve closure member 37 preferably consists completely of plastic, more preferably of a single plastic material, which is flexible and permeable to sterilisation gases. By way of example, the valve closure member 37 may consist of EPM, EPDM, FPM or the like. It preferably has a plate portion 38, which preferably has a slightly convexly curved sealing face and is provided at its periphery with an axially protruding annular edge 39. Between the edge 39 and a central hub portion 40, the plate portion 38 preferably has an annular spring zone 41, which can be formed by an annular groove surrounding the hub 40 remote from the convexly curved side. The spring zone 41 enables a slight resilience of the comparatively more rigid edge 39 with respect to the hub portion 40, which is likewise rigid, in the axial direction. The resilient deformation takes place predominantly in the spring zone 41. The spring zone also acts as a permeation zone, in which the wall thickness at most is a few tenths of a millimeter. Sterilisation gases can penetrate the spring zone 41 in sufficient quantity in order to cause sterilisation.

A central pin 42 extends away from the hub portion 40, preferably concentrically in the axial direction, wherein the central pin 42 protrudes into one of the channels departing from the valve chamber 30, for example into the pump channel 23, without blocking said pump channel. The central pin 42 can be used as an orientation and assembly aid.

The convex end face of the valve closure member 37 is associated with a valve seat 43, which for example is formed by an annular bead and surrounds the suction channel 16. The valve seat 43 can be formed by a round rib, as illustrated in the example according to FIG. 2. This, together with the resilience of the plastic of the valve closure member 37, causes an extensive sealing contact between the valve closure member 37 and valve seat 43. The diameter of the valve seat 43 is preferably at most as large as the diameter of the spring zone 41. In addition, both are preferably arranged concentrically with one another.

An overflow structure 44 is associated with the valve closure member 37. This structure is arranged in the valve chamber 30, preferably on the side opposite the valve seat 43. The overflow structure 44, as indicated in FIG. 2, can be formed by radial grooves 45, of which one or more extend radially outwardly starting from the pump channel 23. The diameter of the edge 39 is smaller then the diameter of the valve chamber 30. Liquid can thus flow axially over the plate portion 38.

The pump unit 10 described in this regard functions as follows:

During operation, the pump pistons 25, 29 are moved alternately to and fro. The pump piston 25 or 29 moving in the direction of a volume enlargement of the pump cylinder 22 or 26 then sucks in sodium chloride solution via the suction channel 16. The valve closure member 37 is moved away here from the valve seat 43 with slight deformation of the spring zone 41 and also optionally further parts, in order to unblock the passage.

In modified embodiments, the valve chamber 30 and the valve closure member 37 can also be matched to one another such that the valve closure member 37 has slight axial play. In this case too, the suction movement of the respective pump piston 25 or 29 leads to the opening of the inlet valve 18 or 19 in question.

If, by contrast, one of the piston pumps 25, 20 runs in the direction of volume reduction of the pump cylinder 22, 26, the liquid pressure and flow causes a closure of the respective inlet valve 18, 19 and an opening of the respective outlet valve 20, 21, which is formed in accordance with the inlet valves 18, 19. The structural difference lies merely in that the valve seat 43 is not arranged on the first housing part 14, but on the second housing part 15, in order to surround the pump channel 24 or 28. Accordingly, the overflow structure 44 is associated with the housing part 14 and is arranged at the base of the valve chamber recess 31.

The pump unit 10 described in this regard is produced as follows:

The housing parts 14, 15 are first provided and the valve closure members 34 are then fitted onto the housing part 15 illustrated in FIG. 6. The valve closure members 37 are each placed here onto the corresponding extensions 33 in the orientation predefined by FIG. 1. The first housing part 14 is then fitted via its valve chamber recesses 31 onto the extensions 33. The first housing part contacts the annular shoulders 46 formed on the extensions 33 before the underside of said housing part has reached the upper end face 34. Annular ultrasonic weld seams or friction weld seams 36 (FIG. 1) are now formed on the shoulders 46 by means of ultrasound effect.

Following assembly, the pump unit 10 is sterilised with or without pump pistons 25, 29. To this end, the principle of gas sterilisation is preferably applied, in which the housing parts 14, 15 preferably consisting of plastic are exposed to no temperature load or are exposed to an insignificant temperature load. When flushing the pump unit 10 with sterilisation gas, this gas is fed into the suction channel 16 and/or the pressure channel 17 for example via the connections 11, 12. Here, the gas can easily open the inlet valves 18, 19 and/or the outlet valves 20, 21 and/or can pass through the thin plastic membrane by diffusion, in particular in the region of the hub portion 41. A reliable sterilisation of the pump unit 10 is thus possible.

Numerous modifications are possible on the described pump unit 10. By way of example, the overflow structure 44, as illustrated in FIGS. 4 and 5, can be formed by recesses 47, which are formed in the edge 39 of the valve closure member 37. By contrast, in this embodiment a planar closed bearing surface 48 can be associated with the edge 39 and forms the end face of the extension 33 or of the valve chamber closure 32. It is also noted that the channel 16 in the vicinity of the valve seat 43, as illustrated, can be formed by a number of individual channels or also by a single channel of larger cross section. Further modifications are possible.

The pump unit 10 according to the invention has a particularly simple structure, which includes merely two housing parts 14, 15 and also four valve closure members 37 and pump pistons 25, 29. The valve closure members 37 are preferably identical to one another and are trapped in a pocket between both housing parts 14, 15. The housing parts 14, 15 are preferably permanently interconnected by means of an ultrasonic weld seam. The valve closure members are formed by disc-like or plate-like plastic parts resilient per se, which may optionally have a central pin 42 as an assembly and orientation aid. As desired, the valve closure members can bear with or without bias against their respective valve seat 43 and can form valves which open and close particularly reliably, are responsive to the slowest flow velocities and can be easily sterilised.

LIST OF REFERENCE SIGNS 10 pump unit
11 connection to the NaCl store
12 connection to the instrument for water jet surgery
13 housing
14 first housing part
15 second housing part
16 suction channel
17 pressure channel
18 suction valve
19 suction valve
20 outlet valve
21 outlet valve
22 first pump cylinder
23, 24 pump channels of the first pump cylinder 22
25 pump piston
26 second pump cylinder
27, 28 pump channels
29 pump piston
30 valve chamber
31 valve chamber recess
32 valve chamber closure
33 extension
34 upper end face of the second housing part 15
35 annular gap
36 friction weld seam
37 valve closure member
38 plate portion
39 edge
40 hub portion
41 spring zone
42 central pin
43 valve seat
44 overflow structure
45 radial grooves
46 annular shoulder
47 recess
48 bearing surface

What is claimed is:

1. A pump unit (10) for water jet surgery, comprising:
a pump housing (13), which has a first housing part (14) and a second housing part (15), wherein
a suction channel (16) and a pressure channel (17) are formed in the first housing part (14), wherein the pressure channel (17) is configured to connect to a water jet surgery instrument,
at least two pump cylinders (22, 26), which are formed on the second housing part (15) and which are configured to receive pump pistons (25, 29) and from each of which two pump channels (23, 24; 27,28) depart,
valve chamber recesses (31), which are formed in one of the housing parts (14, 15),
valve chamber closures (32), which are associated with the valve chamber recesses (31) in order to shut off said valve chamber recesses so as to form respective valve chambers (30), into which the pressure channel (17) or the suction channel (16) leads,
at least one valve closure member (37), which is permeable to sterilization gas,
wherein the suction channel (16), the pressure channel (17) and the pump channels (23, 24, 27, 28) are in communication with select ones of the respective valve chambers (30);
wherein the valve chamber closure (32) is formed together with an edge (39) of the valve closure member (37) and one or more recesses (47) defined in the valve closure member (37) in a manner defining an overflow structure (44) that defines a path for the sterilization gas to contact at least portions of opposing sides of the valve closure member (37) while the valve closure member (37) is in a closed position preventing liquid flow between the respective valve chamber (30) and a corresponding one of the pressure channel (17) or the suction channel (16);
wherein the at least one valve closure member (37) includes a centrally located hub portion (40) and a spring zone (41) located between the centrally located hub portion (40) and the edge (39), wherein the spring zone (41) is of a reduced thickness relative to the centrally located hub portion (40) and the edge (39) for allowing resilient deformation of the valve closure member at the spring zone (41).

2. The pump unit according to claim 1, wherein the valve closure member (37) comprises a plate portion (38) and a central pin (42) and is arranged in one of the respective valve chambers (30) such that the central pin (42) extends into one of the suction channel (16), the pressure channel (17) and the pump channels (23, 24, 27, 28), wherein the plate portion (38) is configured to deform to open and close a fluid passage through one of the respective valve chambers (30).

3. The pump unit according to claim 1, wherein the valve chamber closures (32) are formed as extensions (42) protruding into the valve chamber recesses (31).

4. The pump unit according to claim 1, wherein the valve chamber closures (32) with the valve chamber recesses (31) define an annular gap (35).

5. The pump unit according to claim 1, wherein the housing parts (14, 15) are interconnected by an integrally bonded connection (36).

6. The pump unit according to claim 5, wherein the connection (36) is a friction weld seam.

7. The pump unit according to claim 5, wherein the connection (36) is arranged in a plane beyond which extensions (33) protrude.

8. The pump unit according to claim 1, wherein each valve chamber closure (32) defines one of the pump channels (23, 24, 27, 28).

9. The pump unit according to claim 1, wherein at least two of said valve chamber closures (32) are associated with each pump cylinder (22, 26), one of said valve chamber closures having one of the pump channels (23, 27) serving as an inlet channel and another of said valve chamber closures having another one of the pump channels (24, 29) serving as an outlet channel.

10. The pump unit according to claim 9, wherein a central pin (42) of the valve closure member (37) is arranged to protrude into the suction channel (16) or into the pump channel (23, 27) serving as the inlet channel.

11. The pump unit according to claim 9, wherein a valve seat (43) is formed at the pump channel (24, 28) that leads to the pressure channel (17).

12. The pump unit according to claim 11, wherein the valve closure member (37) is arranged to bear against the valve seat (43) without play.

13. The pump unit according to claim 1, wherein the suction channel (16) opens out at a valve seat (43), against which the valve closure member (37) bears without play.

14. The pump unit according to claim 1, wherein identical valve closure members of the at least one valve closure member (37) are arranged in the respective valve chambers (30).

15. The pump unit according to claim 1, wherein the valve closure member (37) has a convexly curved surface on one of the opposing sides thereof for engaging with a valve seat (43), and the spring zone (41) is formed at least in part by an annular groove formed on the other of the opposing sides of the valve closure member (37), the annular groove extending about the centrally located hub portion (40).

16. The pump unit according to claim 15, wherein the valve seat (43) has a diameter and the annular groove has a diameter that is at least as large as the diameter of the valve seat.

17. A pump unit (10) for water jet surgery, comprising:
a pump housing (13), which has a first housing part (14) and a second housing part (15), wherein
a suction channel (16) and a pressure channel (17) are formed in the first housing part (14), wherein the pressure channel (17) is configured to connect to a water jet surgery instrument,
at least two pump cylinders (22, 26), which are formed on the second housing part (15) and which are configured to receive pump pistons (25, 29) and from each of which two pump channels (23, 24; 27,28) depart,
valve chamber recesses (31), which are formed in one of the housing parts (14, 15),
valve chamber closures (32), which are associated with the valve chamber recesses (31) in order to shut off said valve chamber recesses so as to form respective valve chambers (30), into which the pressure channel (17) or the suction channel (16) leads,
at least one valve closure member (37) having a flexible disc or plate like shape and is configured to deform to open and close a fluid passage through one of the respective valve chambers (30),
wherein the suction channel (16), the pressure channel (17) and the pump channels (23, 24, 27, 28) are in communication with select ones of the respective valve chambers (30);
wherein at least one of the valve chamber closures (32) is formed together with an edge (39) of an associated valve closure member of the valve closure members (37) and one or more recesses (47) defined by the associated valve closure member in a manner defining an overflow structure (44) that defines a path for a sterilization gas to contact at least portions of opposing sides of the associated valve closure member (37) while the associated valve closure member (37) is in a closed position preventing liquid flow between the respective valve chamber (30) and a corresponding one of the pressure channel (17) or the suction channel (16);
wherein the at least one valve closure member (37) includes a centrally located hub portion (40) and a spring zone (41) located between the centrally located hub portion (40) and the edge (39), wherein the spring zone (41) is of a reduced thickness relative to the centrally located hub portion (40) and the edge (39) for allowing resilient deformation of the valve closure member at the spring zone (41).

18. The pump unit according to claim 17, wherein the flexible disc or plate like shape of the at least one valve closure member (37) comprises a plate portion (38) and a central pin (42) and is arranged in one of the respective valve chambers (30) such that the central pin (42) extends into one of the suction channel (16), the pressure channel (17) and the pump channels (23, 24, 27, 28).

19. The pump unit according to claim 18, wherein the central pin (42) of the valve closure member (37) is arranged to protrude into the suction channel (16) or into the pump channel (23, 27) serving as the inlet channel.

20. The pump unit according to claim 17, wherein at least two of said valve chamber closures (32) are associated with each pump cylinder (22, 26), one of said valve chamber closures having one of the pump channels (23, 27) serving as an inlet channel and another of said valve chamber closures having another one of the pump channels (24, 29) serving as an outlet channel.

\* \* \* \* \*